United States Patent
Kanamori et al.

(10) Patent No.: US 7,179,945 B2
(45) Date of Patent: Feb. 20, 2007

(54) HIGH-SELECTIVE PRODUCTION METHOD OF DI(AMINOMETHYL)-SUBSTITUTED AROMATIC COMPOUND

(75) Inventors: Yoshinori Kanamori, Niigata (JP); Shuji Ebata, Niigata (JP); Kengo Tsukahara, Niigata (JP); Yoshiaki Yamamoto, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 513 days.

(21) Appl. No.: 10/781,884

(22) Filed: Feb. 20, 2004

(65) Prior Publication Data
US 2005/0277790 A1 Dec. 15, 2005

(30) Foreign Application Priority Data
Feb. 20, 2003 (JP) ............................. 2003-042397

(51) Int. Cl.
*C07C 211/00* (2006.01)
(52) U.S. Cl. ...................................... 564/384
(58) Field of Classification Search ................ 564/384
See application file for complete search history.

(56) References Cited

U.S. PATENT DOCUMENTS

| | | | |
|---|---|---|---|
| 3,647,054 A | 3/1972 | Tsuboi et al. | |
| 6,476,267 B1 | 11/2002 | Fuchigami et al. | |

FOREIGN PATENT DOCUMENTS

| | | |
|---|---|---|
| DE | 77 983 | 12/1970 |
| EP | 0 908 447 A1 | 4/1999 |
| EP | 1449825 A1 * | 8/2004 |
| JP | 51024494 | 2/1976 |
| JP | 09040630 | 2/1997 |
| JP | 10204048 | 8/1998 |
| JP | 2002-205980 | 7/2002 |
| JP | 2003-327563 | 11/2003 |
| WO | WO 96/18603 | 6/1996 |

OTHER PUBLICATIONS

Abstract of JP Patent No. 48022593, dated Jul. 6, 1973.
Abstract of JP Patent No. 38008719, dated Jun. 11, 1963.

* cited by examiner

*Primary Examiner*—Samuel Barts
(74) *Attorney, Agent, or Firm*—Antonelli, Terry, Stout and Kraus, LLP.

(57) ABSTRACT

A di(aminomethyl)-substituted aromatic compound is produced by a two-stage hydrogenation. In the first stage, an aromatic dinitrile is hydrogenated into a cyano(aminomethyl)-substituted aromatic compound in the presence of a Pd-containing catalyst. The resultant cyano(aminomethyl)-substituted aromatic compound is then hydrogenated in the second stage into the target di(aminomethyl)-substituted aromatic compound in the presence of a Ni- and/or Co-containing catalyst. By the above method, the di(aminomethyl)-substituted aromatic compound is produced in a high selectivity and a sufficiently high yield without reducing the catalyst life.

5 Claims, No Drawings

HIGH-SELECTIVE PRODUCTION METHOD OF DI(AMINOMETHYL)-SUBSTITUTED AROMATIC COMPOUND

BACKGROUND OF THE INVENTION

1. Field of the Invention

The present invention relates to a production method of a di(aminomethyl)-substituted aromatic compound by the hydrogenation of an aromatic dinitrile. The di(aminomethyl)-substituted aromatic compound is useful as the raw material for producing hardeners, synthetic resins, isocyanates, etc.

2. Description of the Prior Art

It has been proposed to hydrogenate an aromatic dinitrile in the presence of catalyst system containing various metals. For example, Japanese Patent Publication No. 51-24494 proposes a production method of 3-cyanobenzylamine or 4-cyanobenzylamine by the palladium-catalyzed hydrogenation of isophthalonitrile or terephthalonitrile in the presence of liquid ammonia and an inorganic alkali. Japanese Patent Application Laid-Open Nos. 9-40630 and 10-204048 propose production methods of aromatic cyanomethylamine (cyano(aminomethyl)-substituted aromatic compound) by hydrogenating one of the nitrile groups in an aromatic dinitrile in the presence of a nickel and/or cobalt-containing Raney catalyst. These patent documents only relate to the production of the aromatic cyanomethylamine, and describe nothing about the production of a diamine (di(aminomethyl)-substituted aromatic compound) corresponding thereto.

Japanese Patent Publication No. 10-502671 discloses a semi-hydrogenation of an aliphatic dinitrile into a corresponding aliphatic aminonitrile in the presence of a catalyst selected from the group consisting of Raney nickel catalysts containing a doping element such as zinc and elements in groups IVb, VIb, VIIb and VIII of the periodic table and Raney cobalt catalysts containing a doping element such as zinc and elements in groups IVb, VIb, VIIb and VIII of the periodic table. Japanese Patent Application Laid-Open No. 2001-524464 proposes a continuous partial hydrogenation of an aliphatic dinitrile into a corresponding aliphatic aminonitrile in a heterogeneous system in the presence of a hydrogenation catalyst. These patent documents only relate to the partial hydrogenation of the aliphatic dinitrile into the aliphatic aminonitrile, and describe nothing about the partial hydrogenation of the aromatic dinitrile into the aromatic cyanomethylamine and the subsequent hydrogenation of the aromatic cyanomethylamine into the corresponding diamine (di(aminomethyl)-substituted aromatic compound).

It has been further proposed to convert the aromatic dinitrile to the corresponding diamine (di(aminomethyl)-substituted aromatic compound) by a single step hydrogenation in the presence of a Ni- or Co-containing catalyst. For example, Japanese Patent Publication No. 38-8719 proposes the hydrogenation of phthalonitrile into the target xylylene diamine in alcohol containing a slight amount of water in the presence of a Raney nickel or Raney cobalt catalyst doped with caustic alkali. Japanese Patent Publication No. 48-22593 proposes the production of xylylene diamine from phthalonitrile in the presence of a supported nickel catalyst containing magnesium oxide as the co-catalyst. However, these methods fail to produce the target diamine in a sufficiently high yield because of the formation of by-products.

SUMMARY OF THE INVENTION

An object of the present invention is to provide a novel method for producing the di(aminomethyl)-substituted aromatic compound in a high selectivity.

As a result of extensive study in view of the above object, the inventors have found that the target di(aminomethyl)-substituted aromatic compound can be produced in a high selectivity by a two-stage hydrogenation comprising a first stage where an aromatic dinitrile is hydrogenated into an intermediate compound (cyano(aminomethyl)-substituted aromatic compound) of the target compound in the presence of a Pd-containing catalyst, and a second stage where the cyano(aminomethyl)-substituted aromatic compound is hydrogenated into the di(aminomethyl)-substituted aromatic compound in the presence of a Ni- and/or Co-containing catalyst. The present invention has been accomplished on the basis of this finding.

Thus, the present invention provides a method of producing a di(aminomethyl)-substituted aromatic compound represented by the following formula I:

$$NH_2CH_2—R—CH_2NH_2 \qquad (I)$$

wherein R is a bivalent aromatic group and optionally substituted by a group inert to hydrogenation, by a two-stage hydrogenation comprising a first stage of hydrogenating an aromatic dinitrile represented by the following formula II:

$$CN—R—CN \qquad (II)$$

wherein R is the same as defined above, into a cyano(aminomethyl)-substituted aromatic compound represented by the following formula III:

$$NH_2CH_2—R—CN \qquad (III)$$

wherein R is the same as defined above, in the presence of a catalyst X containing Pd, and a second stage of hydrogenating the cyano(aminomethyl)-substituted aromatic compound of the formula III from the first stage into the di(aminomethyl)-substituted aromatic compound in the presence of a catalyst Y containing Ni and/or Co.

DETAILED DESCRIPTION OF THE INVENTION

The present invention will be described below in more detail.

The starting aromatic dinitrile is represented by the following formula II:

$$CN—R—CN \qquad (II).$$

R is a bivalent aromatic group such as phenylene group, naphthylene group, etc. The positions of two cyano groups on the aromatic group are not particularly limited, for example, may be any one of o-, m- and p-position if the aromatic group is phenylene group. The aromatic group may be substituted by a group inert to the hydrogenation such as alkyl group, alkoxyl group, halogen, amino group, amido group and hydroxyl group. Generally, the reactivity of the aromatic dinitrile in the hydrogenation is largely changed by the substituent group on the aromatic ring. In the method of the present invention, however, the hydrogenation proceeds efficiently even in the presence of such a substituent group. The aromatic dinitrile preferably used in the present invention may be phthalonitrile, isophthalonitrile, terephthalonitrile and 1,5-dicyanonaphthalene.

Hydrogen to be used in the hydrogenation of the present invention is not required to be specifically purified, and hydrogen of industrial grade is sufficient for the purpose. The hydrogen partial pressure in the reaction system is preferably 2.0 to 20.0 MPa for both the first and second stage hydrogenation. Within the above range, the target diamine is preferably produced in sufficiently high yield and the use of a high-pressure reactor can be avoided to preferably reduce production costs.

In the first stage hydrogenation, the aromatic dinitrile of the formula II is hydrogenated into the cyano(aminomethyl)-substituted aromatic compound represented by the following formula III:

$$NH_2CH_2—R—CN \quad\quad\quad (III)$$

wherein R is the same as defined above, in the presence of a catalyst X containing Pd.

The hydrogenation is performed preferably in liquid phase. The solvent to be used is not particularly limited as far as it is an inert organic solvent which is not reduced by hydrogen. Examples thereof include alcohol solvents such as methanol, ethanol and propyl alcohol; hydrocarbon solvents such as m-xylene, mesitylene and pseudocumene; and ether solvents such as dioxane. The inert organic solvent is preferably used in an amount of 1.0 to 99.0 parts by weight per one part by weight of the aromatic dinitrile. To prevent the formation of by-product, liquid ammonia may be used as the solvent alone or in a mixture with the inert organic solvent mentioned above. The amount of liquid ammonia to be used is preferably 0.5 to 99 parts by weight per one part by weight of the aromatic dinitrile. Within the above range, the lowering of the yield of cyano(aminomethyl)-substituted aromatic compound due to the formation of by-product and the lowering of the space time yield can be preferably prevented. The mixing ratio of the inert organic solvent to liquid ammonia, if used, is preferably 0.01 to 99.0 by weight.

The first stage hydrogenation may be performed in either batch or continuous manner. The reaction temperature is preferably 20 to 150° C. Within this range, the yield of target compound is preferably increased because the conversion of the starting aromatic dinitrile is high and the by-production of high-boiling compound is prevented.

The contact time between the staring aromatic dinitrile and the catalyst X is preferably 0.01 to 10.0 h, although depending on the kind of the starting compound, the charged amounts of the starting compound, solvent and hydrogen, the reaction temperature and the reaction pressure.

The catalyst X used in the first stage for hydrogenating the aromatic dinitrile into the corresponding cyano(aminomethyl)-substituted aromatic compound may be a known catalyst containing Pd. Generally, a catalyst containing Pd supported on $Al_2O_3$, $SiO_2$, diatomaceous earth, $SiO_2$—$Al_2O_3$ or $ZrO_2$, preferably $Al_2O_3$, is used as the catalyst X. The supported amount of Pd is preferably 0.05 to 10% by weight based on the catalyst X. The amount of the catalyst X to be used is, in terms of Pd, 0.0001 to 0.1 part by weight per one part by weight of the starting aromatic dinitrile. If the hydrogenation is performed in a fixed bed flow reactor, the flow rate of the starting aromatic dinitrile is preferably 1.0 to 2000 $h^{-1}$ per unit weight of Pd. By using the catalyst X in an amount within the above range, the hydrogenation proceeds efficiently without increasing the catalyst cost.

In the second stage hydrogenation, the cyano(aminomethyl)-substituted aromatic compound from the first stage is hydrogenated into the di(aminomethyl)-substituted aromatic compound represented by the following formula I:

$$NH_2CH_2—R—CH_2NH_2 \quad\quad\quad (I)$$

wherein R is the same as defined above, in the presence of a catalyst Y containing Ni and/or Co.

The hydrogenation is performed preferably in liquid phase. The solvent to be used is not particularly limited as far as it is an inert organic solvent which is not reduced by hydrogen. Examples thereof include alcohol solvents such as methanol, ethanol and propyl alcohol; hydrocarbon solvents such as m-xylene, mesitylene and pseudocumene; and ether solvents such as dioxane. The inert organic solvent is preferably used in an amount of 1.0 to 99.0 parts by weight per one part by weight of the cyano(aminomethyl)-substituted aromatic compound. To prevent the formation of by-product, liquid ammonia may be used as the solvent alone or in a mixture with the inert organic solvent mentioned above. The amount of liquid ammonia to be used is preferably 0.5 to 99 parts by weight per one part by weight of the cyano(aminomethyl)-substituted aromatic compound. Within the above range, the lowering of the yield of di(aminomethyl)-substituted aromatic compound due to the formation of by-product and the lowering of the space time yield can be preferably prevented. The mixing ratio of the inert organic solvent to liquid ammonia, if used, is preferably 0.01 to 99.0 by weight.

The second stage hydrogenation may be performed in either batch or continuous manner. The reaction temperature is preferably 20 to 150° C. Within this range, the yield of target compound is preferably increased because the conversion of the cyano(aminomethyl)-substituted aromatic compound is high and the by-production of high-boiling compound is prevented.

The contact time between the cyano(aminomethyl)-substituted aromatic compound and the catalyst Y is preferably 0.01 to 10.0 h, although depending on the kind of the starting compound, the charged amounts of the starting compound, solvent and hydrogen, the reaction temperature and the reaction pressure.

The catalyst Y used in the first stage for hydrogenating the cyano(aminomethyl)-substituted aromatic compound into the corresponding di(aminomethyl)-substituted aromatic compound may be a known catalyst containing Ni and/or Co. Generally, a catalyst prepared by supporting Ni and/or Co on $Al_2O_3$, $SiO_2$, diatomaceous earth, $SiO_2$—$Al_2O_3$ or $ZrO_2$ by a precipitation method, Raney Ni catalyst or Raney Co catalyst is preferably used as the catalyst Y The supported amount of the catalytic metal (Ni and/or Co) is preferably 5.0 to 90.0% by weight based on the catalyst Y The amount of the catalyst Y to be used is, in terms of the catalytic metal, 0.1 to 2.0 parts by weight per one part by weight of the starting cyano(aminomethyl)-substituted aromatic compound. If the hydrogenation is performed in a fixed bed flow reactor, the flow rate of the starting cyano(aminomethyl)-substituted aromatic compound is preferably 0.05 to 5.0 $h^{-1}$ per unit weight of the catalytic metal. By using the catalyst Y in an amount within the above range, the hydrogenation proceeds efficiently without increasing the catalyst cost.

If the first stage hydrogenation is performed in a reactor other than fixed bed reactor, the reaction product solution should be separated from the catalyst X before the resultant cyano(aminomethyl)-substituted aromatic compound is subjected to the second stage hydrogenation. The use of the same solvent in the first stage and the second stage makes the production efficient, because the reaction product solution as separated after the first stage hydrogenation can be directly used in the second stage hydrogenation.

The di(aminomethyl)-substituted aromatic compound produced in the second stage hydrogenation is recovered after separated from the solvent and the catalyst in known manners. For example, after separating the reaction system into the vapor component and the liquid component, the target compound is recovered from the liquid component by distillation.

In the known production methods of the di(aminomethyl)-substituted aromatic compound, high-boiling by-products which are formed during the reaction adhere to the catalyst thereby to gradually increase the pressure difference. Therefore, the catalyst should be regenerated by decomposing the high-boiling by-products by hydrogenation. Thus, the catalyst life is shortened in the known production methods. In contrast, the catalyst life is prolonged in the production method of the present invention, because the formation of by-products is minimized.

The present invention will be explained in more detail by reference to the following example which should not be construed to limit the scope of the present invention.

Preparation of Ni Catalyst

An aqueous solution of mixed metal salts was prepared by dissolving 305.0 g of nickel nitrate hexahydrate (Ni(NO$_3$)$_2$.6H$_2$O) and 13.6 g of cobalt nitrate hexahydrate (Co(NO$_3$)$_2$.6H$_2$O) in 840 g of pure water at 40° C. Separately, 190.6 g of ammonium hydrogencarbonate (NH$_4$HCO$_3$) was dissolved in 2.4 kg of pure water under sufficient stirring while raising the temperature to 40° C. To the aqueous solution of ammonium hydrogencarbonate, the aqueous solution of mixed metal salts kept at 40° C. was added under sufficient stirring to prepare a precipitation slurry of nickel carbonate. The slurry was heated to 80° C. and kept there for 30 min. Then, the slurry was cooled to 40° C. and kept there. Separately, 118.4 g of zirconium nitrate aqueous solution (Zr content: 25% by weight in terms of ZrO$_2$) was mixed with 300 g of pure water and kept at 40° C. Further, 42.8 g of ammonium hydrogencarbonate (NH$_4$HCO$_3$) was dissolved in 530 g of pure water and kept at 40° C. The aqueous solution of zirconium nitrate and the aqueous solution of ammonium hydrogencarbonate were simultaneously added to the precipitation slurry of nickel carbonate to precipitate zirconium carbonate. The precipitation slurry thus prepared was stirred for 30 min while being kept at 40° C. Then, the precipitation slurry was filtered. The separated precipitation was washed, dried at 110° C. overnight and calcined at 380° C. for 18 h in air. The resultant calcined powder was mixed with 3% by weight of graphite and made into 3.0 mm φ×2.5 mm tablets, which were then reduced at 400° C. in hydrogen stream to prepare catalyst A. The supported amount of Ni in the catalyst A was 65% by weight.

EXAMPLE 1

Hydrogenation of Isophthalonitrile

Into a 100-ml autoclave, were charged 3.2 g of isophthalonitrile, 10.4 g of mesitylene, 10.0 g of liquid ammonia and 2.0 g of Pd-alumina pellets (manufactured by N.E. Chemcat Corporation; Pd content=5% by weight), and the inner pressure was raised to 4.9 MPa by hydrogen gas. Then, the autoclave was shaken at 50° C. until the change of pressure was no longer appreciated. The analysis on the reaction product solution showed that the conversion of isophthalonitrile was 95.7 mol %, the yield of 3-cyanobenzylamine was 87.3 mol % and the yield of m-xylynenediamine was 7.7 mol %. The reaction solution separated from the catalyst was charged into a 100-ml autoclave together with 10.0 g of liquid ammonia and 2.0 g of Ni-diatomaceous earth pellets (manufactured by Nikki Chemical Co., Ltd.; Ni supported amount=46% by weight). The inner pressure was raised to 4.9 MPa by hydrogen gas. Then, the autoclave was shaken at 50° C. until the change of pressure was no longer appreciated. The analysis on the reaction product solution showed that the conversion of isophthalonitrile was 100 mol %, the yield of 3-cyanobenzylamine was 0.2 mol % and the yield of m-xylynenediamine was 89.4 mol %.

EXAMPLE 2

Hydrogenation of Terephthalonitrile

Into a 100-ml autoclave, were charged 3.2 g of terephthalonitrile, 10.4 g of mesitylene, 10.0 g of liquid ammonia and 2.0 g of Pd-alumina pellets (manufactured by N.E. Chemcat Corporation; Pd content=5% by weight), and the inner pressure was raised to 4.9 MPa by hydrogen gas. Then, the autoclave was shaken at 50° C. until the change of pressure was no longer appreciated. The analysis on the reaction product solution showed that the conversion of terephthalonitrile was 94.8 mol %, the yield of 4-cyanobenzylamine was 88.8 mol % and the yield of p-xylynenediamine was 5.8 mol %. The reaction solution separated from the catalyst was charged into a 100-ml autoclave together with 10.0 g of liquid ammonia and 2.0 g of Ni-diatomaceous earth pellets (manufactured by Nikki Chemical Co., Ltd.; Ni supported amount=46% by weight). The inner pressure was raised to 4.9 MPa by hydrogen gas. Then, the autoclave was shaken at 50° C. until the change of pressure was no longer appreciated. The analysis on the reaction product solution showed that the conversion of terephthalonitrile was 100 mol %, the yield of 4-cyanobenzylamine was 0.5 mol % and the yield of p-xylynenediamine was 87.7 mol %.

EXAMPLE 3

Hydrogenation of 1,5-Dicyanonaphthalene

Into a 100-ml autoclave, were charged 3.2 g of 1,5-dicyanonaphthalene, 10.4 g of mesitylene, 10.0 g of liquid ammonia and 2.0 g of Pd-alumina pellets (manufactured by N.E. Chemcat Corporation; Pd content=5% by weight), and the inner pressure was raised to 4.9 MPa by hydrogen gas. Then, the autoclave was shaken at 50° C. until the change of pressure was no longer appreciated. The analysis on the reaction product solution showed that the conversion of 1,5-dicyanonaphthalene was 92.6 mol %, the yield of 1-aminomethyl-5-cyanonaphthalene was 85.4 mol % and the yield of 1,5-diaminomethylnaphthalene was 4.0 mol %. The reaction solution separated from the catalyst was charged into a 100-ml autoclave together with 10.0 g of liquid ammonia and 2.0 g of Ni-diatomaceous earth pellets (manufactured by Nikki Chemical Co., Ltd.; Ni supported amount=46% by weight). The inner pressure was raised to 4.9 MPa by hydrogen gas. Then, the autoclave was shaken at 50° C. until the change of pressure was no longer appreciated. The analysis on the reaction product solution showed that the conversion of 1,5-dicyanonaphthalene was 100 mol %, the yield of 1-aminomethyl-5-cyanonaphthalene was 0.0 mol % and the yield of 1,5-diaminomethylnaphthalene was 88.0 mol %.

EXAMPLE 4

Hydrogenation of Isophthalonitrile

Into a 100-ml autoclave, were charged 3.2 g of isophthalonitrile, 10.4 g of mesitylene, 10.0 g of liquid ammonia and 2.0 g of Pd-alumina pellets (manufactured by N.E. Chemcat Corporation; Pd content=5% by weight), and the inner pressure was raised to 4.9 MPa by hydrogen gas. Then, the autoclave was shaken at 50° C. until the change of pressure was no longer appreciated. The analysis on the reaction product solution showed that the conversion of isophthalonitrile was 95.7 mol %, the yield of 3-cyanobenzylamine was 87.3 mol % and the yield of m-xylynenediamine was 7.7 mol %. The reaction solution separated from the catalyst was charged into a 100-ml autoclave together with 10.0 g of liquid ammonia and 2.0 g of the catalyst A. The inner pressure was raised to 4.9 MPa by hydrogen gas. Then, the autoclave was shaken at 50° C. until the change of pressure was no longer appreciated. The analysis on the reaction product solution showed that the conversion of isophthalonitrile was 100 mol %, the yield of 3-cyanobenzylamine was 0.0 mol % and the yield of m-xylynenediamine was 91.1 mol %.

EXAMPLE 5

Hydrogenation of Terephthalonitrile

Into a 100-ml autoclave, were charged 3.2 g of terephthalonitrile, 10.4 g of mesitylene, 10.0 g of liquid ammonia and 2.0 g of Pd-alumina pellets (manufactured by N.E. Chemcat Corporation; Pd content=5% by weight), and the inner pressure was raised to 4.9 MPa by hydrogen gas. Then, the autoclave was shaken at 50° C. until the change of pressure was no longer appreciated. The analysis on the reaction product solution showed that the conversion of terephthalonitrile was 94.8 mol %, the yield of 4-cyanobenzylamine was 88.8 mol % and the yield of p-xylynenediamine was 5.8 mol %. The reaction solution separated from the catalyst was charged into a 100-ml autoclave together with 10.0 g of liquid ammonia and 2.0 g of the catalyst A. The inner pressure was raised to 4.9 MPa by hydrogen gas. Then, the autoclave was shaken at 50° C. until the change of pressure was no longer appreciated. The analysis on the reaction product solution showed that the conversion of terephthalonitrile was 100 mol %, the yield of 4-cyanobenzylamine was 0.2 mol % and the yield of p-xylynenediamine was 92.1 mol %.

EXAMPLE 6

Hydrogenation of 1,5-Dicyanonaphthalene

Into a 100-ml autoclave, were charged 3.2 g of 1,5-dicyanonaphthalene, 10.4 g of mesitylene, 10.0 g of liquid ammonia and 2.0 g of Pd-alumina pellets (manufactured by N.E. Chemcat Corporation; Pd content=5% by weight), and the inner pressure was raised to 4.9 MPa by hydrogen gas. Then, the autoclave was shaken at 50° C. until the change of pressure was no longer appreciated. The analysis on the reaction product solution showed that the conversion of 1,5-dicyanonaphthalene was 92.6 mol %, the yield of 1-aminomethyl-5-cyanonaphthalene was 85.4 mol % and the yield of 1,5-diaminomethylnaphthalene was 4.0 mol %. The reaction solution separated from the catalyst was charged into a 100-ml autoclave together with 10.0 g of liquid ammonia and 2.0 g of the catalyst A. The inner pressure was raised to 4.9 MPa by hydrogen gas. Then, the autoclave was shaken at 50° C. until the change of pressure was no longer appreciated. The analysis on the reaction product solution showed that the conversion of 1,5-dicyanonaphthalene was 100 mol %, the yield of 1-aminomethyl-5-cyanonaphthalene was 1.5 mol % and the yield of 1,5-diaminomethylnaphthalene was 87.1 mol %.

Comparative Example 1

Hydrogenation of Isophthalonitrile

Into a 100-ml autoclave, were charged 3.2 g of isophthalonitrile, 10.4 g of mesitylene, 10.0 g of liquid ammonia and 2.0 g of the catalyst A, and the inner pressure was raised to 4.9 MPa by hydrogen gas. Then, the autoclave was shaken at 50° C. until the change of pressure was no longer appreciated. The analysis on the reaction product solution showed that the conversion of isophthalonitrile was 95.5 mol % and the yield of m-xylynenediamine was 49.4 mol %.

Comparative Example 2

Hydrogenation of Terephthalonitrile

Into a 100-ml autoclave, were charged 3.2 g of terephthalonitrile, 10.4 g of mesitylene, 10.0 g of liquid ammonia and 2.0 g of the catalyst A, and the inner pressure was raised to 4.9 MPa by hydrogen gas. Then, the autoclave was shaken at 50° C. until the change of pressure was no longer appreciated. The analysis on the reaction product solution showed that the conversion of terephthalonitrile was 94.4 mol % and the yield of p-xylynenediamine was 35.6 mol %.

According to the present invention, the di(aminomethyl)-substituted aromatic compound is produced in a high selectivity and a sufficiently high yield by the two-stage hydrogenation comprising the first stage where the aromatic dinitrile is hydrogenated into an intermediate compound (cyano(aminomethyl)-substituted aromatic compound) of the target compound in the presence of a Pd-containing catalyst, and a second stage where the cyano(aminomethyl)-substituted aromatic compound is hydrogenated into the di(aminomethyl)-substituted aromatic compound in the presence of a Ni- and/or Co-containing catalyst. In addition, the catalyst life is prolonged in the production method of the present invention, because the formation of by-products is minimized. Therefore, by the production method of the present invention, the di(aminomethyl)-substituted aromatic compound is produced from the aromatic dinitrile at low production costs.

What is claimed is:

1. A method of producing a di(aminomethyl)-substituted aromatic compound represented by the following formula I:

NH$_2$CH$_2$—R—CH$_2$NH$_2$    (I)

wherein R is a bivalent aromatic group and optionally substituted by a group inert to hydrogenation, by a two-stage hydrogenation comprising:

a first stage of hydrogenating an aromatic dinitrile represented by the following formula II:

CN—R—CN    (II)

wherein R is the same as defined above, into a cyano(aminomethyl)-substituted aromatic compound represented by the following formula III:

NH$_2$CH$_2$—R—CN       (III)

wherein R is the same as defined above, in the presence of a catalyst X containing Pd; and a second stage of hydrogenating the cyano(aminomethyl)-substituted aromatic compound from the first stage into the di(aminomethyl)-substituted aromatic compound in the presence of a catalyst Y containing Ni and/or Co.

2. The method according to claim 1, wherein the catalyst X comprises 0.05 to 10% by weight of Pd carried on a support.

3. The method according to claim 2, wherein the support is alumina.

4. The method according to claim 1, wherein the catalyst Y is prepared by a precipitation method to carry Ni and/or Co on a support.

5. The method according to claim 1, wherein the catalyst Y is a Raney nickel catalyst of a Raney cobalt catalyst.

* * * * *